US010191008B2

United States Patent
Chapples et al.

(10) Patent No.: US 10,191,008 B2
(45) Date of Patent: Jan. 29, 2019

(54) GAS SENSOR WITH SOLID ELECTROLYTE HAVING WATER VAPOR DIFFUSION BARRIER COATING

(71) Applicant: Life Safety Distribution AG, Hegnau (CH)

(72) Inventors: John Chapples, Portsmouth (GB); Keith Francis Edwin Pratt, Portsmouth (GB); Martin Geoffrey Jones, Havant (GB)

(73) Assignee: Life Safety Distribution AG, Hegnau (CH)

( * ) Notice: Subject to any disclaimer, the term of this patent is extended or adjusted under 35 U.S.C. 154(b) by 360 days.

(21) Appl. No.: 14/577,178

(22) Filed: Dec. 19, 2014

(65) Prior Publication Data
US 2016/0178565 A1    Jun. 23, 2016

(51) Int. Cl.
*G01N 27/407*    (2006.01)
*G01N 27/404*    (2006.01)

(52) U.S. Cl.
CPC ......... *G01N 27/407* (2013.01); *G01N 27/404* (2013.01)

(58) Field of Classification Search
CPC ............ G01N 27/407; G01N 27/4075; G01N 27/4071; G01N 27/4072; G01N 27/4074; G01N 27/4077; G01N 27/4078; G01N 27/406; G01N 27/404
See application file for complete search history.

(56) References Cited

U.S. PATENT DOCUMENTS

| 4,812,221 A * | 3/1989 | Madou | G01N 27/4045 |
| | | | 204/412 |
| 5,281,324 A | 1/1994 | Kiesele et al. | |
| 5,346,604 A * | 9/1994 | Van Sin | G01N 27/404 |
| | | | 204/400 |

(Continued)

FOREIGN PATENT DOCUMENTS

| CN | 107209145 A | 9/2017 |
| EP | 0299779 A2 | 1/1989 |

(Continued)

OTHER PUBLICATIONS

Van Der Wal P D et al: "Extremely stable Nafion based carbon monoxide sensor", Sensors and Acuators B: Chemical: International Journal Devoted to Research and Development of Physical and Chemical Transducers, Elsevier S.A. Ch, vol. 35, No. 1, Sep. 1, 1996, pp. 119-123.

(Continued)

*Primary Examiner* — Gurpreet Kaur
(74) *Attorney, Agent, or Firm* — Wick Phillips Gould & Martin, LLP

(57) ABSTRACT

A gas sensor including a gas sensing electrode, a counter electrode disposed within a housing, and respective conductors that connect the gas sensing electrode to the counter electrode via a sensing circuit is disclosed. The housing includes a solid electrolyte in communication with the gas sensing electrode and counter electrode wherein the solid electrolyte further comprises one or more coatings or layers. The one or more coatings or layers have a lower water vapor transport rate than that of the electrolyte, such that, in use, water vapor transport between the electrolyte and atmosphere is reduced.

18 Claims, 2 Drawing Sheets

Side Elevation of Solid Electrolyte Gas Sensor

(56) References Cited

U.S. PATENT DOCUMENTS

| | | | |
|---|---|---|---|
| 6,890,373 B2* | 5/2005 | Nemoto | B01D 53/02 |
| | | | 210/504 |
| 8,747,636 B2 | 6/2014 | Westmarland et al. | |
| 2002/0029965 A1* | 3/2002 | Ulkem | G01N 27/4071 |
| | | | 204/415 |
| 2003/0106811 A1 | 6/2003 | Prohaska et al. | |
| 2005/0034987 A1 | 2/2005 | Zhou et al. | |
| 2010/0170795 A1* | 7/2010 | Cowburn | G01N 27/404 |
| | | | 204/406 |
| 2012/0228140 A1* | 9/2012 | Westmarland | G01N 33/006 |
| | | | 204/431 |
| 2014/0311905 A1 | 10/2014 | Stetter et al. | |
| 2015/0001076 A1* | 1/2015 | Porro | G01N 33/0027 |
| | | | 204/412 |
| 2015/0075254 A1* | 3/2015 | Sakuma | G01M 15/104 |
| | | | 73/23.31 |

FOREIGN PATENT DOCUMENTS

| | | |
|---|---|---|
| EP | 0366863 A2 | 5/1990 |
| EP | 2498085 A2 | 9/2012 |
| EP | 3234572 A1 | 10/2017 |
| WO | 2016097304 A1 | 6/2016 |

OTHER PUBLICATIONS

PCT/EP2015/080514, PCT International Search Report and Written Opinion, dated Mar. 2, 2016, 16 pages.

PCT/EP2015/080514, PCT Written Opinion of the International Preliminary Examining Authority, dated Nov. 14, 2016, 10 pages.

Parylene From Wikipedia, the free encyclopedia, [retrieved on Oct. 31, 2016]. Retrieved from the Internet:<URL: https://en.wikipedia.org/wiki/Paralyne>, 5 pages.

PCT/EP2015/080514, PCT International Preliminary Report on Patentability, dated Mar. 23, 2017, 22 pages.

* cited by examiner

Plan View of Solid Electrolyte Gas Sensor

Side Elevation of Solid Electrolyte Gas Sensor

Side Elevation of Solid Electrolyte Gas Sensor

GAS SENSOR WITH SOLID ELECTROLYTE HAVING WATER VAPOR DIFFUSION BARRIER COATING

FIELD

The field relates to electrochemical gas sensors for the detection of a target gas in an atmosphere and, more particularly, to oxygen and toxic gas sensors having a solid electrolyte that is coated with a barrier that reduces water vapor loss.

BACKGROUND

Electrochemical sensors traditionally comprise a gas diffusion working electrode, often based on a platinum or graphite/platinum catalyst dispersed on polytetrafluorethylene (PTFE) tape. The target gas is reacted at this electrode while a balancing reaction takes place at the counter electrode. The electrodes are contained within an outer housing which contains a liquid electrolyte, such as sulfuric acid. The gas typically enters the housing through a controlled diffusion access port, which regulates the ingress of target gas into the cell. The gas reacts at the electrode and affects the electrical output of the sensor.

Conventional electrochemical gas sensors mostly employ aqueous solutions of acids (typically sulfuric acid) as the electrolyte. Under benign environmental conditions and short excursions into extreme environments, the composition of the electrolyte remains fairly constant and the sensor performance exhibits minimal deviation from calibration. However, prolonged subjection to severely hydrating (high relative humidity, (RH %)) or dehydrating conditions (low RH %) leads to equilibration of the electrolyte with the environmental relative humidity, and consequently a change in the composition of the electrolyte. This manifests as a deviation in sensor performance from calibrated values or, in extreme instances, the failure of the sensor.

Due to the small quantities of acid incorporated in small sized sensors, it is clear that even small amounts of water exchange between the sensor and the environment has the potential to affect the performance to a degree that would be considered unsatisfactory. Water evaporation from the electrolyte is also problematic. It is desirable for the sensor's working lifetime to be as long as possible but moreover it is important that any particular sensor type will consistently continue to work for at least the indicated lifetime. Early failures lead to the need for more frequent sensor replacement, as well as increased monitoring of sensor performance and, ultimately, a loss in confidence in the sensor. Accordingly, there is a need to produce sensors that have a longer lifetime, which maintain an acceptable level of performance under many different operating environments.

BRIEF DESCRIPTION OF THE DRAWINGS

Examples of electrochemical gas sensors and method of manufacture will now be described and contrasted with conventional sensors, with reference to the accompanying drawings, in which.

DETAILED DESCRIPTION

Figure 1:
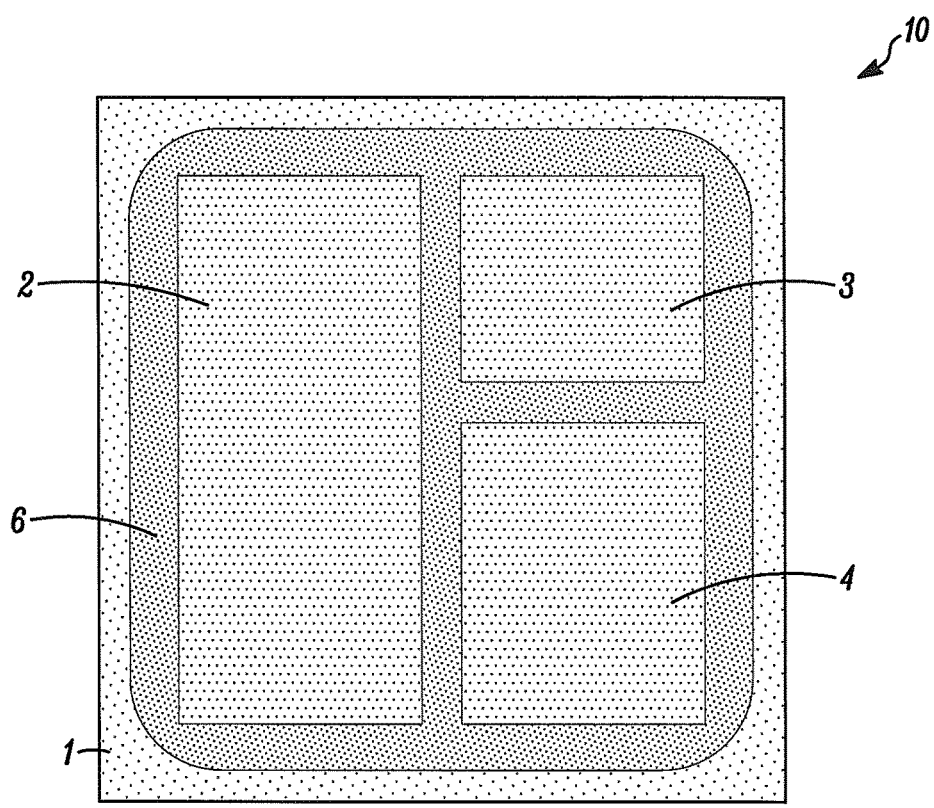
FIG. 1 is a view of an electrochemical gas sensor shown generally in accordance with an illustrated embodiment.

While disclosed embodiments can take many different forms, specific embodiments thereof are shown in the drawings and will be described herein in detail with the understanding that the present disclosure is to be considered as an exemplification of the principles thereof as well as the best mode of practicing same, and is not intended to limit the application or claims to the specific embodiment illustrated.

Solid electrolyte gas sensors usually require a certain amount of water within the solid electrolyte in order to operate properly. Some solid electrolytes incorporate sulfuric acid within a polymer layer to retain sufficient humidity. Due to the small size of these sensors and the small quantity of sulfuric acid present, these sensors have a very low effective reservoir capacity for water. Furthermore, the planar construction of these sensors results in a large surface area of the polymer being exposed to the environment so water transport can be rapid, unless the system is modified as described herein. In order to reduce water ingress and egress in the sensor, a parylene layer alone or a parylene layer in conjunction with a silicone layer can be used to coat the solid electrolyte.

Figure 2:
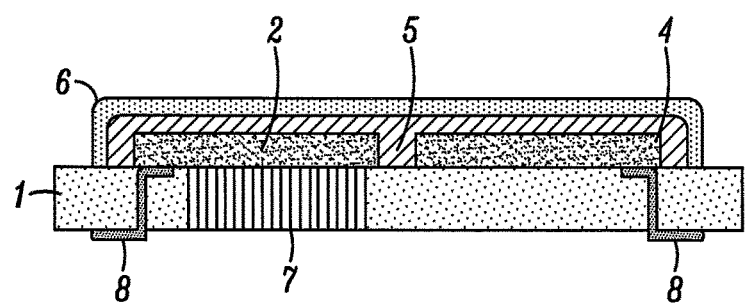
FIG. 2 is a side view of an electrochemical gas sensor shown generally in accordance with an illustrated embodiment.

FIGS. 1 and 2 are a views of an electrochemical gas sensor 10 shown generally, in accordance with one embodiment. The sensor 10 includes a ceramic substrate 1 upon which a gas sensing electrode 2, a reference electrode 3, and a counter electrode 4 are carried. The substrate could be other suitable materials besides ceramics. The electrodes are in contact with a solid or semisolid electrolyte 5 having a coating of a water vapor diffusion barrier 6. The barrier coating may be applied to one or more faces of the solid electrolyte 5. The electrolyte coating 6 can be a parylene layer over a silicone layer or just a parylene layer.

Examples of parylene, i.e., poly(para-xylylene), include "Parylene N" or its substituted derivatives such as, "Parylene C," and "Parylene D." The Parylene "C" coating is para-xylyene with a chlorine atom substituted into its structure. The "C" variant of para-xylylene is applied using a chemical vapor deposition (CVD) process, not requiring "line-of-sight" for the coating at a pressure of 0.1 torr. There are numerous other parylene derivatives that may be suitable including Parylene AM, AF, SF, HT, X, E, VT, CF and more.

Other hydrophobic, chemically resistant barrier coatings are also useful here, provided they perform as a good barrier for inorganic and organic solvents, strong acids, caustic solutions, gases, and water vapor while still allowing sufficient diffusion of oxygen to ensure that the platinum reference electrode can correctly operate as a platinum/oxygen electrode, and for the counter electrode to have sufficient oxygen present to maintain the counter reaction of oxygen reduction. If these conditions are not met, for example if a completely hermetic barrier is used, then the reference potential can drift and/or the counter electrode may change its mechanism to hydrogen evolution rather than oxygen reduction in order to pass the required sensor current. Neither of these effects is desirable. Suitable barrier materials are therefore those with a high ratio of oxygen to water transport, for example fluorinated polymers or polymers such as polypropylene, polyethylene etc. In cases where the electrolyte contains sulfuric acid as a humidification material, unless this can be isolated from the barrier material then the latter also needs to be chemically stable in the presence of the high acid concentrations that can exist under very dry conditions. Materials such as polypropylene and fluorinated polymers are therefore preferred.

Other features of the barrier coating include demonstrating electrical isolation with high tension strain and low dielectric constant, being micropore and pin-hole free, exhibiting thermal and mechanical stability, having very low permeability to gases, and demonstrating high electrical impedance. The barrier coating can be deposited over a layer of silicone. The barrier layer is on the outer surface of the silicone layer that directly covers the solid electrolyte. The barrier coating can have a thickness of one to fifty micrometers. In another embodiment, the barrier coating comprises a thickness of less than ten micrometers.

The electrodes are disposed within a housing, and a means for connecting the electrodes to a sensing circuit, such as a conductor are provided. The housing and ceramic substrate 1 are provided with capillary holes 7 for gas ingress and egress.

By providing the solid electrolyte with a layer or coating of a material with a relatively low water transport rate, it becomes possible to reduce the dehydration of the electrolyte without compromising the sensor design. It should also be noted that the layer or coating also operates to reduce absorption of water by the sensor. This can be important in high humidity environments to eliminate the possibility of a sensor taking on water and bursting in extreme circumstances.

As such, depletion of the electrolyte can be substantially reduced (relative to conventional sensors) while retaining a small sensor footprint and sufficient internal capacity. The lifetime of the sensor is prolonged, and in addition it becomes possible to use the sensor in more extreme environments (i.e. hotter and/or drier) than previously possible.

In one embodiment, the housing comprises acrylonitrile butadiene styrene (ABS) or a polyphenylene oxide (PPO)/ polystyrene (PS) blend. These materials have been found to have the desired properties for manufacture of the sensor, and in particular are well adapted for ultrasonic welding and laser drilling.

The sensor may operate with only two electrodes, with the counter electrode also acting as a reference electrode, but in other embodiments, the sensor further comprises a reference electrode, in which case the sensor can operate on the three electrode principle.

The present description also provides a method of manufacturing an electrochemical gas sensor for the detection of a target gas in an atmosphere, the method comprising: forming a housing comprising integral walls defining a cavity; inserting a barrier coated solid electrolyte within the cavity; providing a gas sensing electrode, a reference electrode, and a counter electrode within the housing, and connecting the electrodes to a sensing circuit, wherein water vapor transport from the electrolyte to the atmosphere is reduced. The concepts discussed here could equally be applied to other sensor types, including toxic gas sensors.

The gas sensing electrode 2 typically comprises a catalyst such as platinum or carbon, supported on a PTFE membrane. Conductive leads (not shown in FIG. 1, element 8 in FIG. 2) are provided to electrically connect the catalytic area to the connection pins. In other sensor types, such as toxic gas sensors, the counter electrode may comprise a catalyst mounted on a PTFE backing tape, in the same manner as the gas sensing electrode 2.

Figure 3:
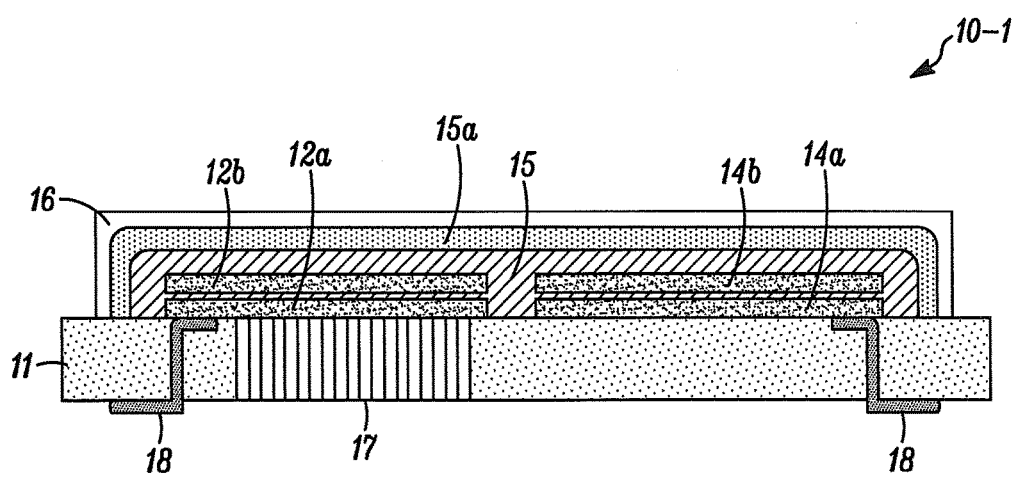
FIG. 3 is a side elevation of another embodiment of a gas sensor.

FIG. 3 shows a side cross sectional view of another implementation 10-1 hereof. In this variant the electrodes are formed from two layers shown as 12a and 12b or 14a and 14b. The gap between layers a and b is shown for illustrative purposes only, the layers are printed in contact with each other with no gap in practice from either a single material or two different materials. The electrolyte layer 15 may partially flow into electrode layers 12b and 14b, to an extent depending on the porosity, physical dimensions and chemical properties of 12b and 14b and the properties of the electrolyte. In some embodiments, the layers 12a and 14a may not be flooded by the electrolyte layer 15, depending on whether these layer have a different physical of chemical property e.g. a different hydrophobicity. In some embodiments, water present within the sensor during normal operation can therefore wet the electrode regions 12b and 14b to maximize the three phase interface region and hence maximize electrode activity, whereas the more hydrophobic nature of electrode regions 12a and 14a prevent water from flooding and potentially blocking the gas access capillaries 17.

FIG. 3 also shows an additional 'humidification' layer 15a which is deposited between the main electrolyte layer 15 and the outer protective and/or water vapor barrier 16. Layer 15a acts as a reservoir for water allowing the electrolyte layer 15 and electrode layers 12b and 14b to remain hydrated to ensure correct operation under dry ambient conditions, without either the electrolyte layer 15 or the electrode layers being prone to flooding under conditions of high humidity. This can be achieved by adding a hygroscopic additive, for example sulfuric acid, to the humidification layer 15a but not to layer 15. This has the additional benefit that the properties of layer 15 and the electrodes can be optimized for their electrochemical performance without having to be chemically resistant to sulfuric acid (which can become highly concentrated in low humidity), whereas the humidification layer 15a can be comprised of a material that is optimized for compatibility with the hygroscopic additive but does not need to perform any electrochemical function. The humidification layer 15a effectively ensures that the electrolyte layer 15 and electrodes are in contact with a continuous source and sink of humidity as required.

The electrodes may, for example, comprise platinum or platinum and carbon and are mixed with PTFE or NAFION® or GEFC-IES (a trademarked perfluorinated ion membrane precursor from the company Golden Energy Fuel Cell) or similar. Differing degrees of hydrophobicity can be achieved by tailoring the ratios of metal to polymer in the electrode formulations.

The electrolyte layer 15 may comprise PAMPS [poly(2-acrylamido-2-methyl-1-propanesulfonic acid)] or NAFION® or GEFC-IES or similar.

The humidification layer 15a may comprise Polyvinylpyrrolidone (PVP) mixed with sulfuric acid and water. Other polymers and acids or other water retaining species can also be used.

Although FIG. 3 shows the presence of two layers for all electrodes and two electrolyte layers, it is also possible to use combinations of either two layers for any or all of the electrodes and one or two layers for the electrolyte.

From the foregoing, it will be observed that numerous variations and modifications may be effected without departing from the spirit and scope hereof. It is to be understood that no limitation with respect to the specific gas sensor illustrated herein is intended or should be inferred. It is, of course, intended to cover by the appended claims all such modifications as fall within the scope of the claims. Further, logic flows depicted in the figures do not require the particular order shown, or sequential order, to achieve desirable results. Other steps may be provided, or steps may be eliminated, from the described flows, and other components may be add to, or removed from the described embodiments.

We claim:

1. A gas sensor comprising:
   (a) a housing;
   (b) a ceramic substrate having a capillary extending through the ceramic substrate, and at least one of a sensing electrode, a reference electrode, or a counter electrode disposed on a first surface;
   (c) solid electrolyte in contact with the at least one of the sensing electrode, the reference electrode, or the counter electrode;
   (d) a barrier coating disposed over the solid elect wherein the barrier coating encapsulates the at least one of the sensing electrode, the reference electrode, or the counter electrode and the solid electrolyte, wherein the barrier coating comprises a layer of silicone and a layer of parylene, wherein the layer of parylene is on the outer surface of the layer of silicone, wherein the layer of silicone directly covers the solid electrolyte.

2. The gas sensor as in claim 1, wherein the gas sensor comprises an electrochemical gas sensor, wherein the electrochemical gas sensor comprises an oxygen sensor or a toxic gas sensor.

3. The gas sensor as in claim 1, wherein the barrier coating has a thickness of one to fifty micrometers.

4. The gas sensor as in claim 1, wherein the solid electrolyte comprises poly(2-acrylamido-2-methyl-1-propanesulfonic acid).

5. The gas sensor as in claim 1, wherein the barrier coating comprises a thickness of less than ten micrometers.

6. The gas sensor as in claim 1, wherein the housing comprises acrylonitrile butadiene styrene (ABS).

7. The gas sensor as in claim 1, wherein the housing comprises a polyphenylene oxide (PPO)/polystyrene (PS) blend.

8. A gas sensor comprising:
   (a) a housing;
   (b) a selected substrate having on one surface a capillary, and on another surface at least one of a sensing electrode, a reference electrode, and a counter electrode;
   (c) a solid electrolyte in contact with at least one of the sensing electrode, the reference electrode, and the counter electrode;
   (d) a humidification layer applied to a surface of the solid electrolyte displaced from the at least one of the sensing electrode, the reference electrode, and the counter electrode by the solid electrolyte, wherein the humidification layer comprises a hygroscopic additive, wherein the solid electrolyte does not contain the hygroscopic additive; and
   (e) a water vapor barrier layer that overlays the humidification layer, wherein the water vapor barrier layer comprises a layer of silicone and a layer of parylene, wherein the layer of parylene is on the outer surface of the layer of silicone.

9. The sensor as in claim 8, wherein the substrate comprises a ceramic.

10. The sensor as in claim 8, wherein the substrate carries at least two of the sensing electrode, the reference electrode, and the counter electrode.

11. A method of manufacturing an electrochemical gas sensor for the detection of a target gas in an atmosphere, the method comprising:
    forming a humidification layer on a solid electrolyte, wherein the humidification layer comprises a hygroscopic additive, wherein the solid electrolyte does not contain the hygroscopic additive;
    forming a water vapor barrier layer that overlays the humidification layer;
    providing a gas sensing electrode, a reference electrode, and a counter electrode, and
    connecting the gas sensing electrode, the reference electrode, and the counter electrode to a sensing circuit, wherein the humidification layer is configured to act as a reservoir for water enabling that electrolyte layer and at least one of the sensing electrode, the reference electrode, and the counter electrode to remain hydrated under dry ambient conditions;
    wherein the water vapor barrier layer comprises a layer of silicone and a layer of parylene, wherein the layer of parylene is on the outer surface of the layer of silicone.

12. The method as in claim 11, which includes providing a substrate.

13. The method as in claim 11, which includes providing a ceramic substrate.

14. A gas sensor comprising:
    a substrate;
    at least one electrode carried by the substrate;
    a solid electrolyte, carried by the substrate, in contact with part of the at least one electrode wherein the at least one electrode comprises first and second spaced apart layers, wherein each of the first and second spaced apart layers comprise a metal and a hydrophobic polymer;
    a humidification layer that overlays, at least in part, the solid electrolyte, wherein the humidification layer comprises a hygroscopic additive, wherein the solid electrolyte does not contain the hygroscopic additive; and
    a barrier coating disposed over the humidification layer, wherein the barrier coating comprises a layer of silicone and a layer of parylene, wherein the layer of parylene is on the outer surface of the layer of silicone.

15. The sensor as in claim 14, wherein the humidification layer hydrates one of the first or second spaced apart layers of the at least one electrode.

16. The sensor as in claim 15, wherein the humidification layer hydrates the solid electrolyte.

17. The sensor as in claim 14, wherein the hygroscopic additive corn wises sulfuric acid.

18. The sensor as in claim 14, wherein the humidification layer comprises polyvinylpyrrolidone.

* * * * *